(12) United States Patent
Brenner et al.

(10) Patent No.: US 9,259,580 B2
(45) Date of Patent: Feb. 16, 2016

(54) MEDICAL SYSTEM, PIEZOELECTRIC KIT, RELATED METHODS AND MEDICAL PROCEDURES

(75) Inventors: Alexander Brenner, Haifa (IL); Andrey Segalla, Moscow (RU)

(73) Assignee: PI-Harvest Holding AG, Schaffhausen (CH)

( * ) Notice: Subject to any disclaimer, the term of this patent is extended or adjusted under 35 U.S.C. 154(b) by 274 days.

(21) Appl. No.: 13/814,924

(22) PCT Filed: Aug. 9, 2011

(86) PCT No.: PCT/EP2011/063725
§ 371 (c)(1),
(2), (4) Date: Mar. 27, 2013

(87) PCT Pub. No.: WO2012/020034
PCT Pub. Date: Feb. 16, 2012

(65) Prior Publication Data
US 2013/0226260 A1    Aug. 29, 2013

Related U.S. Application Data

(60) Provisional application No. 61/401,054, filed on Aug. 9, 2010, provisional application No. 61/520,078, filed on Jun. 6, 2011.

(51) Int. Cl.
*A61N 1/362* (2006.01)
*A61N 1/378* (2006.01)
*H01L 41/113* (2006.01)
*H02N 2/18* (2006.01)
*H01L 41/22* (2013.01)
*A61N 1/375* (2006.01)

(52) U.S. Cl.
CPC ............. *A61N 1/362* (2013.01); *A61N 1/3785* (2013.01); *H01L 41/1136* (2013.01); *H01L 41/22* (2013.01); *H02N 2/18* (2013.01); *A61N 1/3756* (2013.01); *Y10T 29/42* (2015.01)

(58) Field of Classification Search
USPC ....................................................... 607/4, 35
See application file for complete search history.

(56) References Cited

U.S. PATENT DOCUMENTS 4,798,206 A    1/1989  Maddison et al.
6,426,585 B1   7/2002  Kohno
(Continued)

FOREIGN PATENT DOCUMENTS

WO    WO 2010/070650 A1    6/2010

OTHER PUBLICATIONS

WIPO, European International Preliminary Examining Authority, International Preliminary Report on Patentability mailed Nov. 26, 2012 in International Patent Application No. PCT/EP2011/063725, 42 pages.

(Continued)

*Primary Examiner* — Carl H Layno
*Assistant Examiner* — Jon Eric C Morales
(74) *Attorney, Agent, or Firm* — Inskeep IP Group, Inc.

(57) ABSTRACT

A system for harvesting of natural power of the heart movement to be deployed entirely inside or outside human heart. The means and the method for the system deployment/extraction are provided. The system is implemented as storage "satellite" container/housing/carrier unit for piezoelectric power generator, power storage and spare volume for transported cardio stimulator devices. The piezoelectric power generator comprises embedding circuits containing the diode bridge, controller, capacitor and a number of piezo-electric elastic ceramic rods—"leaflets", originally strained asymmetrically with accordance to the heart 3D geometry in order to obtain high energy conversion efficiency and high sensitivity to the heart movement. The innovative construction of the piezoelectric generator is applied to piezoelectric transformer based on cantilever bending vibrations.

20 Claims, 7 Drawing Sheets

(56) References Cited

U.S. PATENT DOCUMENTS

2008/0074002 A1    3/2008   Priya et al.
2009/0171408 A1    7/2009   Solem
2010/0063557 A1    3/2010   Imran
2010/0076517 A1    3/2010   Imran

OTHER PUBLICATIONS

WIPO, European International Search Authority, International Search Report mailed Jan. 23, 2012 in International Patent Application No. PCT/EP2011/063725, 7 pages.

MEDICAL SYSTEM, PIEZOELECTRIC KIT, RELATED METHODS AND MEDICAL PROCEDURES

RELATED APPLICATIONS

This application claims priority to International Patent Application No. PCT/EP2011/063725, International Filing Date 9 Aug. 2011, entitled Medical System, Piezoelectric Kit, Related Methods And Medical Procedures, which claims benefit of U.S. Provisional Application Ser. No. 61/401,054, filed Aug. 9, 2010 entitled System For Harnessing Natural Power Of The Heart Movement Using Piezoelectric Micro Generator, Methods Of It's Deployment Inside And Extraction From Human Heart And Application To Piezoelectric Transformer; and U.S. Provisional Application Ser. No. 61/520,078, filed Jun. 6, 2011entitled System For Harnessing Natural Power Of The Heart Movement Using Piezoelectric Micro Generator, Methods Of It's Deployment Inside And Extraction From Human Heart And Application To Piezoelectric Transformer; all of which are incorporated herein by reference in their entireties.

FIELD OF THE INVENTION

This invention pertains in an aspect to the field of electrically operated implantable medical devices. More particularly embodiments relate to a system for harnessing natural power of cardiac muscle movement using a piezoelectric energy converter. Further, the disclosure relates to piezoelectric kits, medical procedures and methods of deployment inside and extraction from a mammal heart. In another aspect the invention relates to piezoelectric energy converters.

BACKGROUND OF THE INVENTION

There are known numerous attempts to deploy in a human heart a piezoelectric source of energy harvesting electrical power in response to the heart movement in order to provide the power supply for pacemakers and other implantable devices.

Already in 1969 a piezoelectric converter of body motion into electrical energy for driving implants in the form of a completely encased piezoelectric cantilever beam was introduced in U.S. Pat. No. 3,456,134, though no way to deploy the container with the beam was described. An obvious disadvantage of this system is the insufficiency of the energy collected by a piezo-element encapsulated in a container to drive a pacemaker as it reacts only on its own derived movement and not on the muscle's. Another difficulty was the requirement for it's implantation inside the heart.

In 1972 it was suggested in U.S. Pat. No. 3,659,615 to use a piezoelectric bimorph encapsulated and implanted in the chest cavity or adjacent to the left ventricle of the heat, with flexing in reaction to muscular movement used to generate electrical power. The patent is mainly devoted to epicardial devices and to their coverage with synthetic or natural materials. A main disadvantage of such an approach is the great surgical impact resulting from the surgical intervention. Also, the life time of epicardial leads is very short, requiring additional surgical interventions.

U.S. Pat. No. 4,690,143 discloses a self-contained power source mounted in a pacing lead in order to generate electrical power for operating the pacing lead. A distinguishing feature of the technology described in this patent is the mounting of the power generation device in a pacing lead comprising a catheter which is inserted intravenously into a human heart. The power is collected while the lead is bending during the heart muscle contraction. The main disadvantages of the system include insufficient power generation for the overall pacemaker functioning by the piezo-element encapsulated in the lead because it reacts only to the derived movement of the lead and not on the muscle itself. Moreover, any movements of objects mounted inside the heart relative to the heart itself are potential sources of thrombus formation.

Further application of piezo-electric power generation to pacemakers was to connect a piezoelectric transformer to power a lead-based sensor, see U.S. Pat. No. 7,203,551 and an energy transmission system, containing a piezo-electric transducer, from an external unit generating magnetic field or acoustic waves to recharge a pacemaker battery, see U.S. Pat. No. 5,749,909. Also, in U.S. Pat. No. 5,431,694 a bio-operated piezo-electric generator in the form of a flexible sheet of poled polyvinylidene fluoride attached in surface-to-surface contiguity with a skeletal number, is proposed to be connected to a pacemaker. The generated AC is rectified to C, which is supplied to the battery on demand. Needless to say that these architectures only make the artificial in body structures and surgical interventions more complicated.

The further progress of piezoelectric technologies, see for example patents U.S. Pat. No. 5,835,996, U.S. Pat. No. 6,655,035B2, US 2005/0052097A1, US 2005/0082949A1, permits one to build highly efficient piezoelectric generators. For the development of piezoelectric transformers, see U.S. Pat. No. 6,707,235 patent and the literature cited there.

The latest state of the art technologies are presented in the following patents:

WO 2010/070650 A1 discloses a piezoelectric generator for low frequency based on a standard bimorph piezoelectric bending energy generator scheme, but does not produce enough energy for in-body appliances. Also, the use of a cantilever beam with a mechanical energy harvesting unit together encapsulated into a closed box, possess the drawbacks of the same kind as described above for U.S. Pat. Nos. 3,456,134 and 4,690,143

US 2010/0076517A1 presents a technology based on a bundle of piezo-electric fibers arranged around a core conductor. The authors state that, when the bundle is deformed, at least one fiber will be deformed sufficiently to generate sufficient energy for the pacemaker or other selected device. This idea does not differ from that behind U.S. Pat. No. 4,690,143. Consequently, it is not possible to get 20 mW and not more then 50-100 μW can be harvested using such a configuration.

WO 2007/1068284 A1 contains a broad description of the possible applications of the energy harvesting technologies inside and outside the heart. The piezo-electric part is under-developed and is citing the work of Roundy, 2003 where 200 μW were produced from 1 cm cube of the cantilever beam at 120 Hz frequency, considerably less than the 20 mW at 1 Hz needed from, at maximum, a 0.3 cm cube. Consequently, the drawback is of the same kind as in the technology described in WO 2010/070650 A1.

Modern batteries can supply the power for pacemakers for 5-7 years and thus there is no real need for additional energy sources inside the heart, however the two-fold architecture containing a pacemaker itself, with the battery implanted outside the heart and pacing leads inserted intravenously into the heart propose certain inconveniences.

The present invention addresses a widely recognized need to eliminate complicated two-fold or even three-fold in-body structures, which cause obvious problems to patients, thus minimizing surgical procedures and providing patients with a lifetime source of energy feeding a pacemaker.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a system, and methods according to the appended patent claims.

The disclosed approach introduces a new architecture comprising a "satellite" carrier or housing for pacemakers and AICDs equipped with a piezoelectric power station providing sufficient power generation to supply these devices during the patient's lifetime without requiring batteries, wires, or pacing leads and eliminating any mechanical motion relative to the heart.

The property of piezo-electric leaves to provide sensing and pacing at the same time provides the possibility to register in-heart multi-channel cardiograms and interior 3-dimensional heart movement. The ability to transmit this data for analysis outside the body can lead to a new branch of cardiological science.

Some embodiments of the present invention relate hence to the harvesting of natural power from heart movement, by means of a piezoelectric generator, in order to use the harvested energy in one or more implanted devices such as pacemakers, defibrillators, cardio-stimulators and sensors.

An underlying idea behind some embodiments of the present invention is to effectively harvest the mechanical energy of heart movement while avoiding any relative movement between the heart and the power station and minimizing the surgical interventions during the installation procedures.

In contrast to the prior art solutions, multiple component architectures are avoided where a pacemaker is positioned outside the heart due to the battery size and is connected with pacing leads positioned inside the heart through a wire system, which causes obvious inconveniences and disturbances to the patients.

By virtue of this provision, a new approach to the overall domain of pacemaker architectures and their deployment/extraction is introduced. According to the current approach, a pacemaker, or any other electrically driven cardiac implantable device, is mounted in a "satellite" container or carrier unit (hereinafter "satellite") containing a piezoelectric power generator and power storage system. The overall construction for delivery or recovery is mounted on a guidewire inside a catheter sheath for introduction or retrieval through the subclavian, jugular or cephalic vein, for example. The "satellite" is transvascularly passed down the vein to or from the desired position at the heart.

For example, the routine locations in the right atrium and right ventricle are the right atrial appendage and the right ventricular apex. Alternatively, the system deployment can be performed in the apex of the left ventricle, right atrium, coronary sinus or other location.

Yet another alternative approach comprises the incorporation of piezoelectric "leaflets," according to some embodiments of the current invention, into a cardiac harnessing system as described in US published patent application 2007/0197859 A1, which can be used as complementary technology allowing to deploy the piezoelectric elements outside the heart and benefit from the heart motion. A cardiac harnessing system according to the '859 publication refers to a device fitted onto a patient's heart and percutaneously applying a compressive force on it. US 2007/0197859 A1 is incorporated herein by reference in its entirety for all purposes.

The "satellite" is finally fixed to the endocardial wall with the help of an anchoring unit, a screw for example, on its distal portion, e.g. its front surface. The anchoring unit may have various shapes for providing the anchoring function. Suitable shapes are for instance that of a threaded screw, a corkscrew helical shape with one or more helical elements, an anchor unit having barbs or hooks, etc. Fibrous tissue surrounding the screw will eventually integrate itself into the cardiac wall, providing for a stable attachment of the overall construction as the released piezoelectric elastic rods—"leaflets" are pressed to their positions on the ventricle walls by virtue of the SMA rods bridging the "leaflets" with the "satellite".

A system is thus disclosed for the harvesting of power from natural heart movement to be deployed entirely inside or outside the human heart. The means and the method for deploying and retrieving the system are provided. The system is implemented as a storage "satellite" container/housing for a piezoelectric power generator, power storage and spare volume for transported cardio stimulator devices. The piezoelectric power generator comprises embedding circuits containing a diode bridge, controller, capacitor and a number of piezoelectric elastic ceramic rods—"leaflets", originally strained asymmetrically with accordance to the heart 3D geometry in order to obtain high energy conversion efficiency and high sensitivity to heart movement.

The innovative construction of the piezoelectric generator is applied to a piezoelectric transformer based on cantilever bending vibrations. In some embodiments, the developed technique for construction of a piezoelectric generator is applied to a low frequency piezoelectric transformer based on cantilever bending vibrations capable of lowering the input voltage.

The present invention can be implemented in its various embodiments as a system for harnessing the natural power of heart movement and dispatching the accumulated harnessed power to transported devices such as a pacemaker, a defibrillator and/or other cardio stimulator devices. Examples of such devices are Medtronic Kappa ®900, Vitatron® C-Series, and the EnPulse™ pacemakers. The present invention also contains the methods for the "leaflets" polarization of the system deployment and extraction.

According to an aspect, a medical system is provided for harvesting power from movement of a heart muscle of a heart. The system is deployable at a heart, preferably in its entirety. The system includes a piezoelectric power generator, a power storage unit, a control unit, and an electrically operated medical device, operatively connected to each other and arranged in a carrier unit, namely the "satellite". The piezoelectric power generator comprises a plurality of piezoelectric elastic elongate rod units, herein referred to as "leaflets", for apposition to the heart muscle for generating electric power from the heart muscle movement and for providing sensor signals related to a 3D movement of the heart muscle. Further, resilient connecting units are arranged between the elongate rod units and the carrier unit for providing a pre-tension towards the heart muscle for supporting the apposition.

According to another aspect, a method of manufacturing such piezoelectric elastic elongate rod units is provided. The method comprises polarization of the piezoelectric elastic elongate rod units, comprising separation groups of the electrodes not containing the one belonging to the isolator plate plane into two groups lying above and below an isolator plate plane.

According to yet another aspect, a piezoelectric kit is provided that includes at least one multiple layer bender type piezoelectric element comprising multiple monomorphes for generating electric power under a bending mechanical moment. Each of the monomorphes is separated from its adjacent neighbors by electrodes and polarized in such a way that vectors of polarization of two neighboring layers are anti-linear, and wherein vectors of polarization of two central layers divided by an isolator plate are collinear.

According to yet another aspect, a medical procedure is provided for deployment of a carrier unit at a heart, the carrier unit carrying a piezoelectric power generator, a power storage unit, a control unit, and an electrically operated medical device. The procedure comprises the steps of (a) deploying the carrier unit inside a sheath being attached by means of a proximal end to a capturing unit, such as a claw, being arranged at a distal end of a delivery unit, such as a guidewire of a standard sheath of interventional cardiology, for releasably attaching the carrier unit to the capturing unit, (b) endovascularly transporting the carrier unit to an appropriate heart region inside the sheath by means of guidewire manipulations (c) orienting the carrier unit by means of the guidewire manipulations inside the heart according to fiducial marks on the capturing unit and the delivery unit, such as visible on ultra-sound or fluoroscopy equipment (d) anchoring, such as by screwing, of the carrier nit into the heart muscle by means of a tissue anchoring unit, such as a screw on the distal end of the carrier unit and the guidewire manipulations (e) releasing the carrier unit from the capturing unit of the delivery unit, and (f) extracting of the sheath from the heart and the body.

According to yet another aspect, a medical procedure is provided for extraction of a carrier unit from a heart, the carrier unit carrying a piezoelectric power generator, a power storage unit, a control unit, and an electrically operated medical device. The procedure comprises the steps of (a) endovascularly introducing the sheath with a capturing unit on a distal end of a delivery unit, such as a guidewire into a heart region having implanted therein the carrier unit;

(b) orienting the capturing unit relative to the carrier unit proximal capturing unit through superposition of fiducial marks visible on ultra-sound or fluoroscopy equipment;

(c) capturing of the capturing unit by corresponding capturing unit on the delivery unit;

(d) unscrewing of the carrier unit from the heart muscle with the help of a guidewire manipulation;

(e) introducing the carrier unit back into the sheath together with piezoelectric elastic elongate rod units attached to the carrier unit by resilient connecting elements; and (f) extracting the catheter from the heart and the body together with the carrier unit.

Some embodiments of the invention provide for a single implantable system avoiding multiple components connected by leads.

Some embodiments of the invention also provide for efficient kinetic production of energy from heart muscle movement.

Some embodiments of the invention provide for one or more of the following advantages:

1. The use of any mechanical devices (Swiss watches, "bimorph hammers") is eliminated as well as motion relative to the heart itself, thus making the whole approach less traumatic and harmful, compared with catheter based technologies.

2. The system does not contain batteries. The state of the art technologies are based on the electric power produced by batteries, which are subject to change each several years and resulting in additional surgical interventions.

3. The system does not contain wires. The state of the art technologies contain wires transporting electric power from the batteries placed outside the heart to the sensors placed inside the heart. This leads to complex and repeated surgical interventions, especially for junior patients due to their natural growth.

4. The system does not contain pacing leads. The "satellite" itself contains a screw on its front side, substituting a pacing lead. Also the "leaflets" can be supplied with additional electrodes for pacing of the interventricular septum and other domains accordingly to their sensing process.

5. The system serves as a patients' life-long device. Once installed there is no need for additional surgical interventions for battery changing or wire lengthening.

6. In emergency cases, the system can be safely extracted via a sheath of the same kind as the one used during the installation.

7. The system is able to accumulate almost all acceptable heart 3D dynamics as well as the energy of the blood flow by means of a piezoelectric generator. The extra energy produced by the generator can be used not only by a pacemaker but also by an implanted defibrillator.

8. The system achieves high-level electric power production due to the high-capacity piezoceramic elastic materials used in 3D piezoelectric modules comprising pacemaker "leaflets" and the original architecture of the monolithic multiple layer bender type piezoelectric elements. The "leaflets" are 3-5 times more productive than the state of the art products, and have a lifetime without the loss of piezoelectric properties comparable with the life span of human beings.

9. The original "leaflet" architecture permits the building of a unique, low frequency piezoelectric transformer capable of lowering the input voltage.

The above listed advantages are beneficial in many medical, industrial (Electricity, Security, Aerospace, Tourism, Telecommunications), Government and Military applications. In the Security industry, for example, the developed technology can be applied to remote security sensors an power suppliers, thin pass microphones and dynamics. In the Aerospace industry it can be applied to remote energy harvesters combined with energy storage and anti-vibration systems. The application of the developed technology is described using its application to the piezoelectric transformer based on cantilever bending vibrations but is not intended to be limited to that application.

In the present description the term "satellite" means the storage container for piezoelectric power generator and other devices to be deployed in the human heart.

The term "leaflet" means each of elastic piezoelectric rods being attached to the "satellite" which is deployed inside the heart and harvests electric energy from the myocardial contraction (heart movement) and simultaneously senses myocardial electrical activity.

The term screw means any anchoring mechanism.

The term 3D means 3-Dimensional.

The term SMA means Shape Memory Alloy. The most common SMA material is Nitinol (nickel-titanium alloy).

The term AICD means Automatic Implantable Cardioverter Defibrillator.

The term AC means Alternating electrical Current.

The term DC means Direct electrical Current.

The term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of, will be apparent and elucidated from the following description of embodiments of the present invention, reference being made to the accompanying drawings, in which.

DESCRIPTION OF EMBODIMENTS

Figure 1:
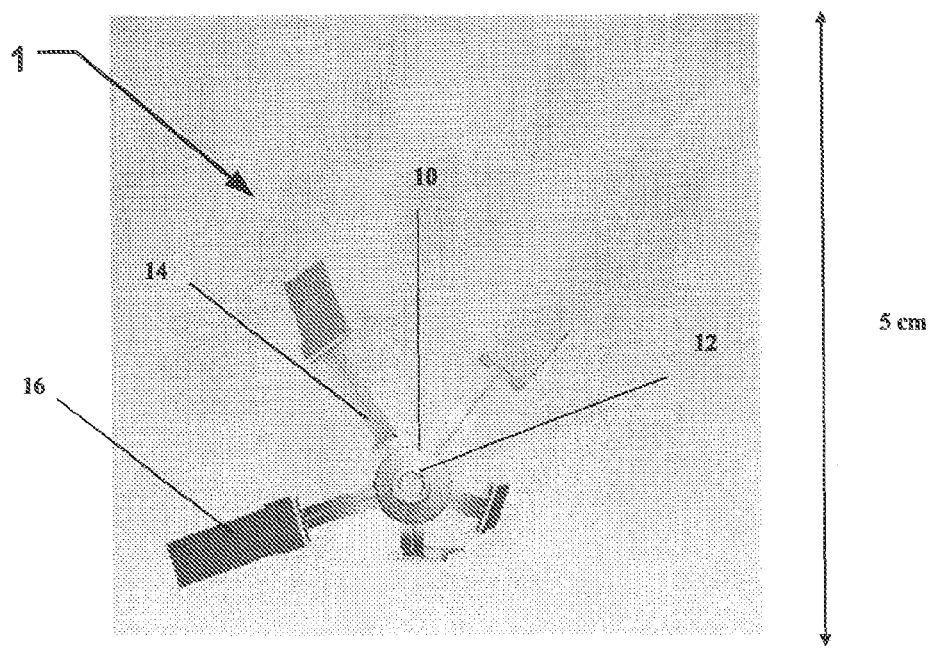
FIG. 1 depicts a schematic illustration of a front view of a harnessing of natural power from the heart movement system.

Specific embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present description of the current invention is given with reference to a pacemaker as an example only. It should be born in mind however that the present invention is not limited strictly to pacemaker, but can be easily adapted to any implantable electrically operated medical implants, such as to defibrillators (AICDs) and any other implantable cardiac devices, as for example, cardiac resynchronization therapy (CRT) devices.

In accordance with one of the embodiments the system comprises:

a) a storage "satellite" container enclosing piezoelectric power generator, power storage and transported devices b) a piezoelectric power generator comprising c) a number of piezoelectric elastic (piezoceramic or other) rods—"leaflets" utilizing monolithic multiple layer bender type piezoelectric elements built of group-wise parallel attached multiple (piezoceramic or other) monomorphes d) the "leaflets" being attached to the "satellite" by means of SMA rods, generate electric power from the heart muscle movement and serve as sensors of the overall 3D heart movements.

e) the SMA rods are mounted on the edge of the "satellite" are in bendable (martensite) state permitting to transport them inside the catheter into the heart (transport position), being released from the catheter turn into rigid springy (austenite) state and press the "leaflets" to the heart interior surface due to their shape memory properties f) the SMA rods are initially configured to reproduce the interior geometry of the interior heart region where the "satellite" has to be placed.

g) embedding circuits containing h) a diode bridge i) a controller microchip comprising a comparator and a voltage regulator j) an electric power storage capacitor k) the "satellite" contains a anchoring mechanism on its front/distal side/aspect for attachment into the heart muscle l) the "satellite" contains a capturing unit on its rear side for the deployment/extraction inside/from a heart m) the capturing unit is as a complement to an external capturing claw attached to the guidewire enclosed into a standard sheath n) the screw and the claw contain marks visible on ultra-sound or fluoroscopy equipment o) the "satellite" and "leaflets", excluding only the screw, are laminated with medical graded silicone rubber.

In accordance with one of the preferred embodiments a method 100 of the "satellite" deployment comprises (a) deployment 110 of the "satellite" inside the standard sheath (b) attachment 120 of the "satellite" rear capturing unit to the claw of the guidewire (c) endovascular transportation 130 of the "satellite" to the right atrial appendage inside the sheath by means of the guidewire manipulations (d) orientation 140 of the "satellite" by means of the guidewire manipulations inside the heart according to the special marks on the said capturing unit and the claw visible on ultra-sound or fluoroscopy equipment (e) screwing 150 of the "satellite" into the heart muscle by means of the screw on the front side and the guidewire manipulations (f) release 160 of the "satellite" from the capturing claw of the guidewire (g) extraction 170 of the catheter together with the "satellite" from the heart and the body.

In accordance with one of the preferred embodiments, a method 200 of the "satellite" extraction comprises:

(a) endovascularly introducing 210 the sheath with the claw on the guidewire into the right atrial appendage where the "satellite" has been previously deployed (b) orienting 220 the claw relative to the "satellite" rear capturing unit through superposition of their marks visible on ultra-sound or fluoroscopy equipment (c) capturing 230 and adjusting 240 the capturing unit by the guidewire claw (d) unscrewing 250 the "satellite" from the heart muscle with the help of the guidewire manipulation (e) pulling 260 the "satellite" back into the sheath together with the flexible "leaflets"

(f) extracting 270 of the catheter together with the "satellite" from the heart and the body.

In accordance with one of the preferred embodiments referring to the piezoelectric "leaflets" it comprises (a) monolithic multiple layer bender type elastic piezoelectric elements comprising in one of preferred embodiments of four piezoelectric strips (monomorphs) denoted below as First, Second, Third and Fourth (see FIG. 6).

(b) each element is built of multiple piezoceramic (or other) monomorphs generating electric power under a bending mechanical moment.

(c) each of the monomorphes is divided from neighboring monomorphs by electrodes and polarized in the way that the vectors of polarization of the two neighboring layers are anti-linear, but the vectors of polarization of the two central layers, divided by an isolator plate, are collinear. According to one of the preferred embodiments, the direction of polarization of the First and Fourth monomorphs is along the narrow dimension of the monomorphs and is opposite to the polarization direction of the Second and Third monomorphs.

Figure 7:
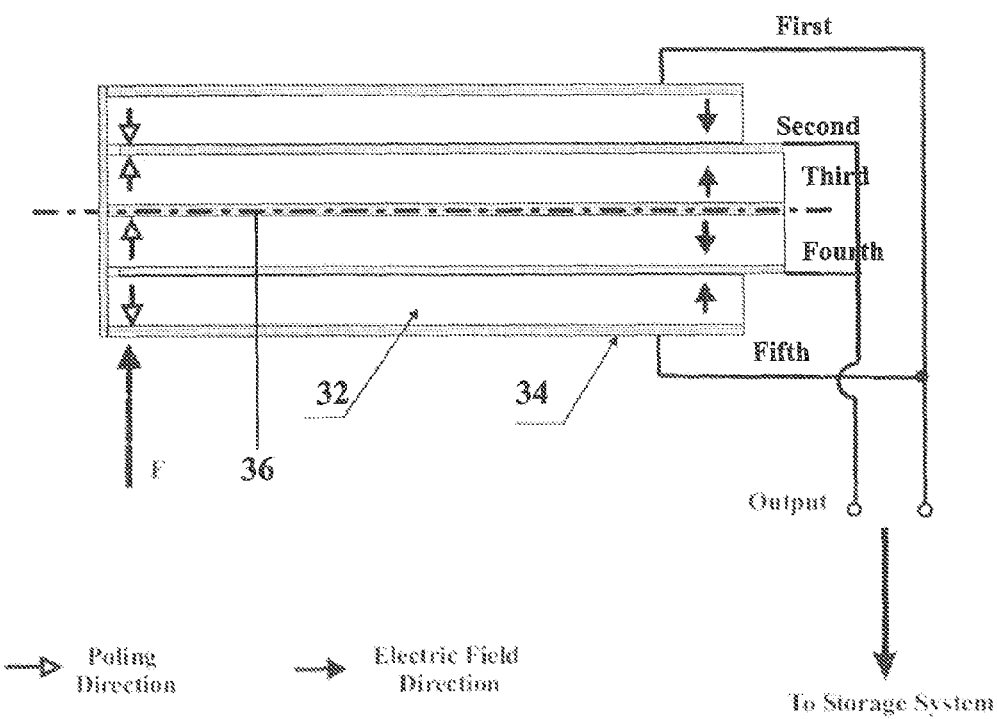
FIG. 7 depicts the power circuit and the polarization directions of the interior "leaflet" structure.

(d) in each "leaflet" all electrodes are divided into two groups and all monomorphes possess two electrodes belonging to different groups. According to one of the preferred embodiments, the bender type piezoelectric element further comprises First, Second, Third, Fourth and Fifth electrodes (see FIG. 7), wherein: the First electrode is located on one the face of the First monomorph, the Second electrode is located between the First and Second monomorphs, the Third electrode is located between the Second and Third monomorphs, the Fourth electrode is located between the Third and Fourth monomorphs, and the Fifth electrode is located on another face of the Fourth monomorph.

(e) According to one of the preferred embodiments, the First, Third and Fifth electrodes are electrically connected to each other and the Second and Fourth electrodes are separately electrically connected to each other.

(f) According to one of the preferred embodiments of the present invention we provide a method of manufacture for "leaflet" polarization comprising the steps of:

i. separating the electrodes (not containing the one belonging to the isolator plate plane) into two groups lying above and below the isolator plate plane;

ii. sequentially polarizing the monomorphs lying above and below the isolator plate plane through application of DC power to each of the electrode group containing the one lying in the isolator plate plane iii. alternatively, simultaneously polarizing the monomorphs through the application of opposite potential DC to each of the monomorph groups, while the group of electrodes containing the one in the isolator plate plane, are connected to the zero potential.

In accordance with one of the preferred embodiments referring to the application of the developed technology to the low frequency piezoelectric transformer, the last comprises (a) two examples of the piezoelectric power generators that are assembled back to back and separated by a passive isolating layer.

The present invention can be implemented in its various embodiments as a system for harnessing of natural power from movement of the heart deployed entirely inside human heart.

In practice, the most common implantable device is a pacemaker deployed in the right ventricle.

It should be born in mi d however, that other implantable devices such as defibrillator would be suitable for implementing the invention instead of, or in addition to a pacemaker, providing that such devices can installed within the "satellite" container. Also, with minor modifications (as additional pacing lead) the system can function in any other part of the heart.

FIG. 1 shows a schematic of an embodiment of a storage "satellite" container (or simply the "satellite") enclosing piezoelectric power generator, power storage and transported devices according to the present invention.

Figure 2:
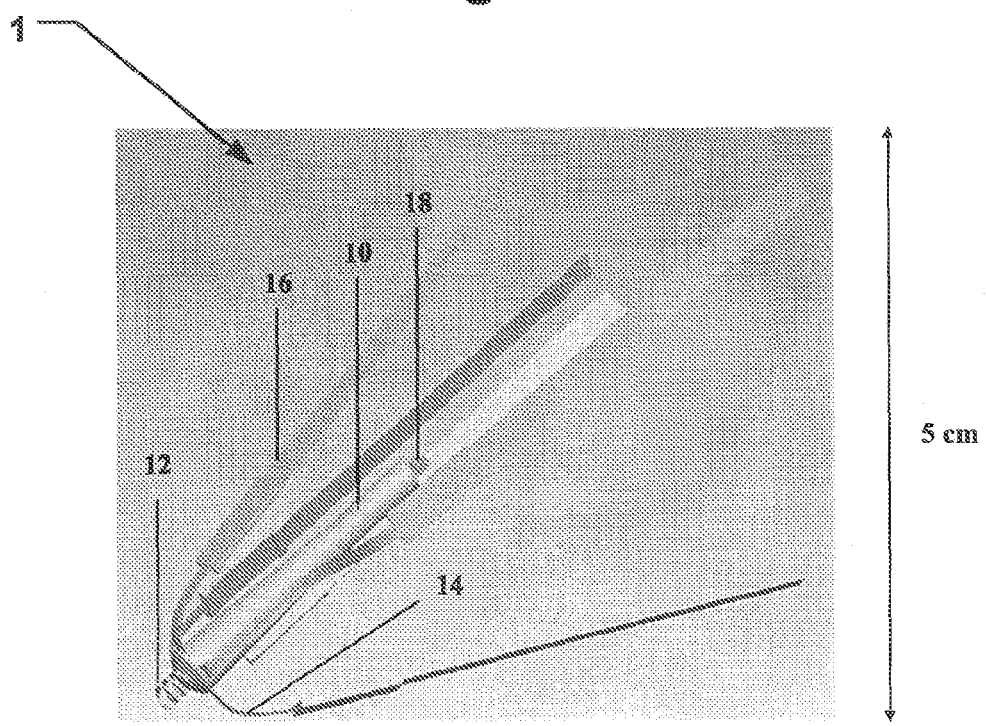
FIG. 2 depicts a schematic illustration of a side view of a harnessing of natural power from the heart movement system.

The system 1 comprising a "satellite" container is designated in e.g. FIGS. 1 and 2 by reference numeral 10. The "satellite" is connected via SMA rods 14 to piezoelectric elastic (piezoceramic or other) rods ("leaflets") 16. The "leaflets" generate electric power from the heart muscle movement of a heart 90. The "leaflets" may in addition serve as sensors of the heart muscle movement at their location. The "leaflets" may thus provide a measurement signal for overall 3D heart movements. The "satellite" is screwed into the heart muscle tissue 95 by means of the anchor (e.g. a screw) 12 on its front side. The measure of 5 cm shown in the Figures is not to be construed as limiting to the invention as defined by the claims, but given as an implementable example of a size range for some embodiments particularly suitable for average adult patients.

Figure 4:
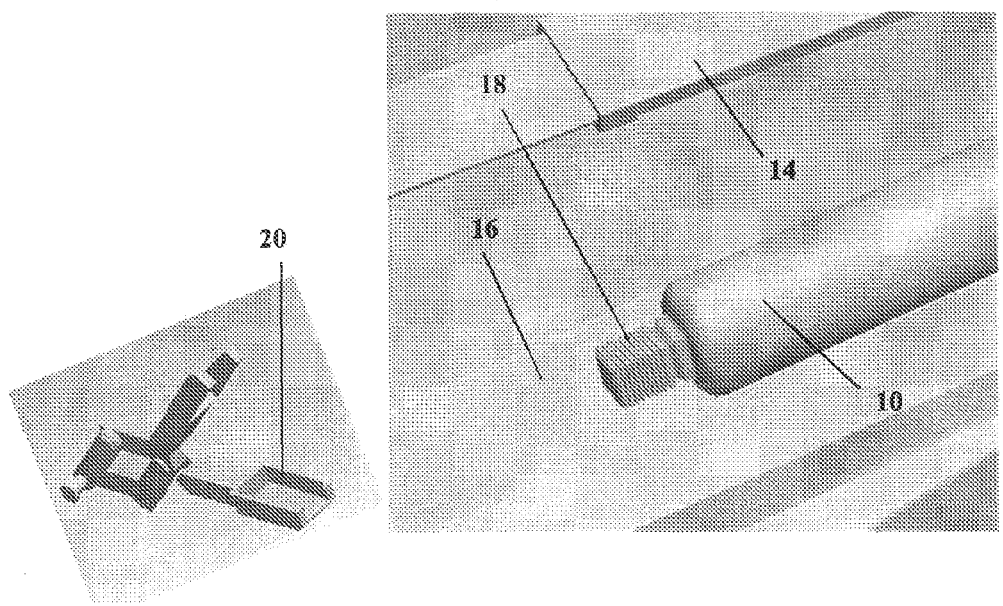
FIG. 4 shows the capturing unit and the capturing claw of the guidewire.

Referring e.g. to FIG. 4, the satellite contains rear capturing unit 18 serving as a complement to an external capturing claw 20 attached to the guidewire encapsulated into a standard sheath.

Figure 5:
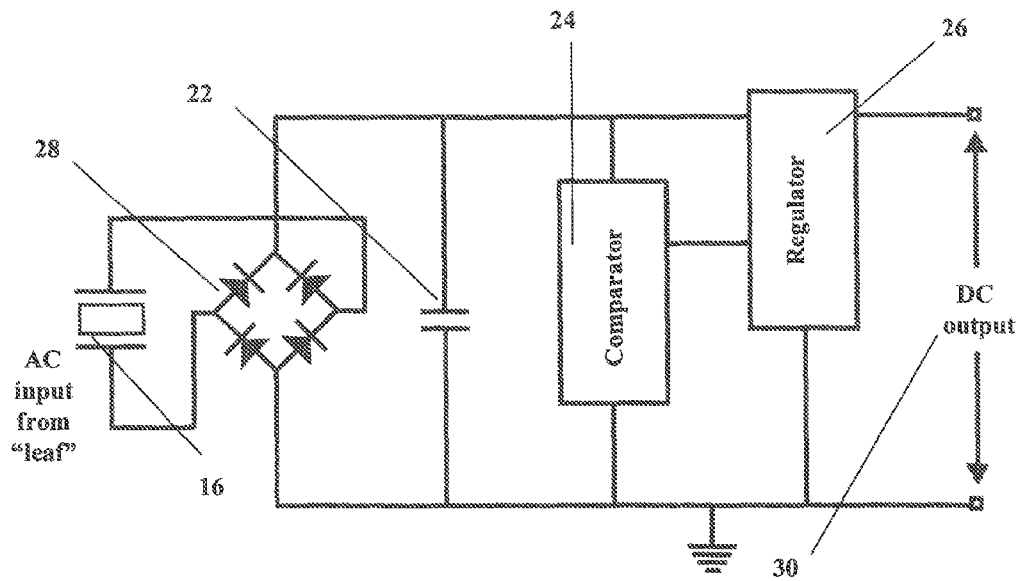
FIG. 5 shows the Schematic Power Circuit.
Figures 12A, 12B:
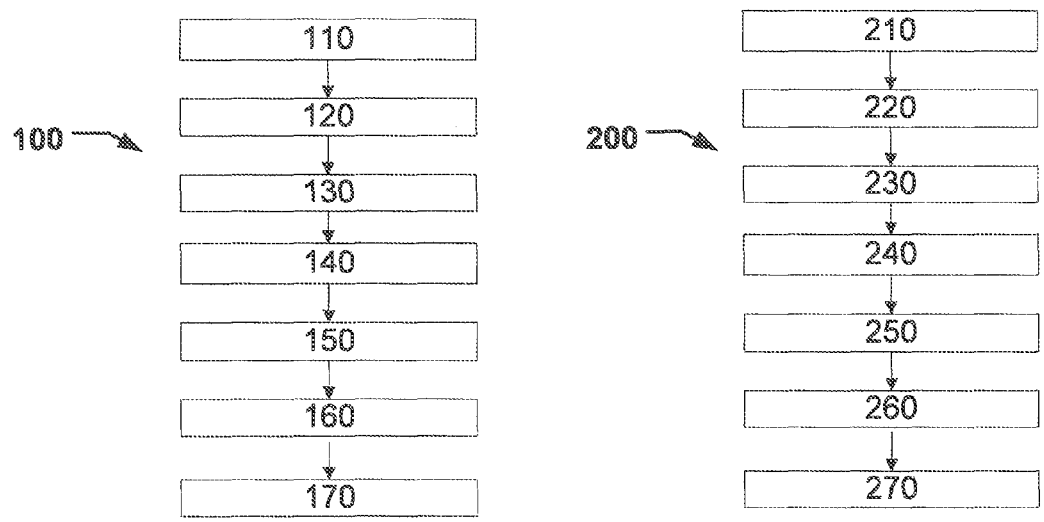
FIGS. 12A and B are flow charts illustrating medical procedures.

The system comprises the piezoelectric power generator partly deployed in the "leaflets" 16, partly inside the "satellite" 10. The overall power circuit is depicted in FIG. 5. Note that this is a particular power conditioning circuit included in this description for the completeness of the exposition only. It will not be further explained in detail as the skilled person will readily understand the circuit components and their function in the context of the present disclosure. In this figure the power circuit of the "leaflet" is denoted as 16. The leaflet circuits are connected with the main circuit through the diode bridge 28. The main circuit comprises an electric power storage capacitor 22, a controller microchip comprising in turn a comparator 24 and a voltage regulator 26 providing a DC pulse to a pacemaker 30.

The interior structure of each "leaflet" comprises monolithic multiple layer bender type elastic piezoelectric elements shown in FIG. 6 and comprising in one preferred embodiment of four piezoelectric strips (monomorphs) denoted below as First, Second, Third and Fourth. Each element is built of multiple piezoceramic (or other) monomorphes 32 generating electric power under a bending mechanical moment. Each of the monomorphes 32 is divided from its neighbors by electrodes 34 and polarized in the way that the vectors of polarization of the two neighboring layers are anti-linear, but the vectors of polarization of the two central layers divided by an isolator plate 36 are collinear, see FIG. 7. According to one of the preferred embodiments, the direction of polarization of the First and Fourth monomorphs is along the narrow dimension of the monomorphs and is opposite to the polarization direction of the Second and Third monomorphs.

In each "leaflet" all electrodes are divided into two groups and all monomorphes possess two electrodes belonging to different groups. According to one of the preferred embodiments, the bender type piezoelectric element further comprises First, Second, Third, Fourth and Fifth electrodes (see FIG. 7), wherein: the First electrode is located on one the faces of the First monomorph, the Second electrode is located between the First and Second monomorphs, the Third electrode is located between the Second and Third monomorphs, the Fourth electrode is located between the Third and Fourth monomorphs, and the Fifth electrode is located on another face of the Fourth monomorph. According to one of the preferred embodiments, the First, Third and Fifth electrodes are electrically connected to each other and the Second and Fourth electrodes are separately electrically connected to each other.

Figure 8:
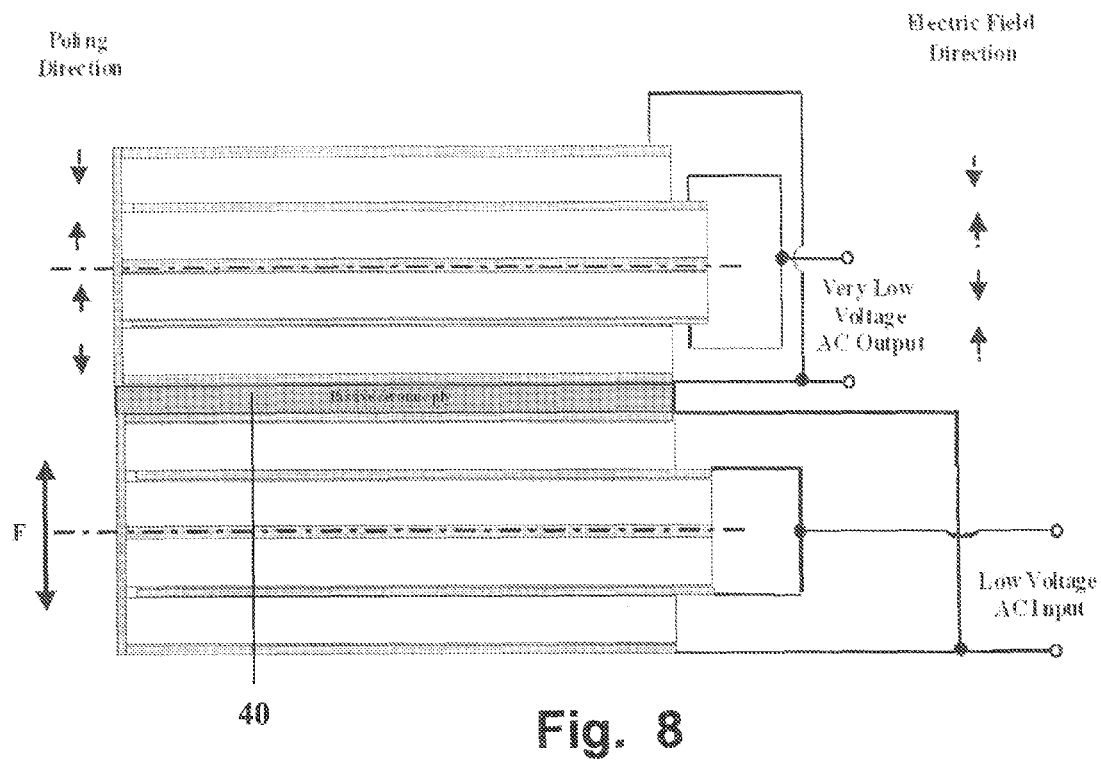
FIG. 8 shows a couple of monolithic multiple layer bender type piezoelectric elements forming a lowering piezoelectric transformer.

As application of above developed "leaflet" structure we get a low frequency (>50 Hz) piezoelectric transformer, see FIG. 8, based on cantilever bending vibrations being a pair of monolithic multiple layer bender type piezoelectric elements separated by passive isolator (ceramic or other) layer 40. As usual, the transformer operates by converting electrical energy into mechanical energy while the input "Leaflet" of the transformer performs as an actuator. This mechanical energy, in the form of a vibration close to the acoustic resonance of the "leaflet", is mechanically transferred to the output "leaflet" of the transformer while bending it. The second half of the transformer then reconverts the mechanical energy into electrical energy working as an above-described generator 16. The uniqueness of the transformer is contained in its Voltage-lowering properties (as an example only, the input voltage can be 50-1000 VAC and the output voltage can be 1-25 VAC). In real life the architecture of the transformer can contain several pairs of "leaflets" in order to utilize a number of necessary input/output voltage relations. Such piezoelectric transformers may be particularly useful in applications within avionics, pipelines, or domestic appliances where 50-60 Hz are readily available. Frequencies in the 20 Hz range are for instance found in pipeline inspection gauges, which can be an application field for both generators and transformers.

Figure 11:
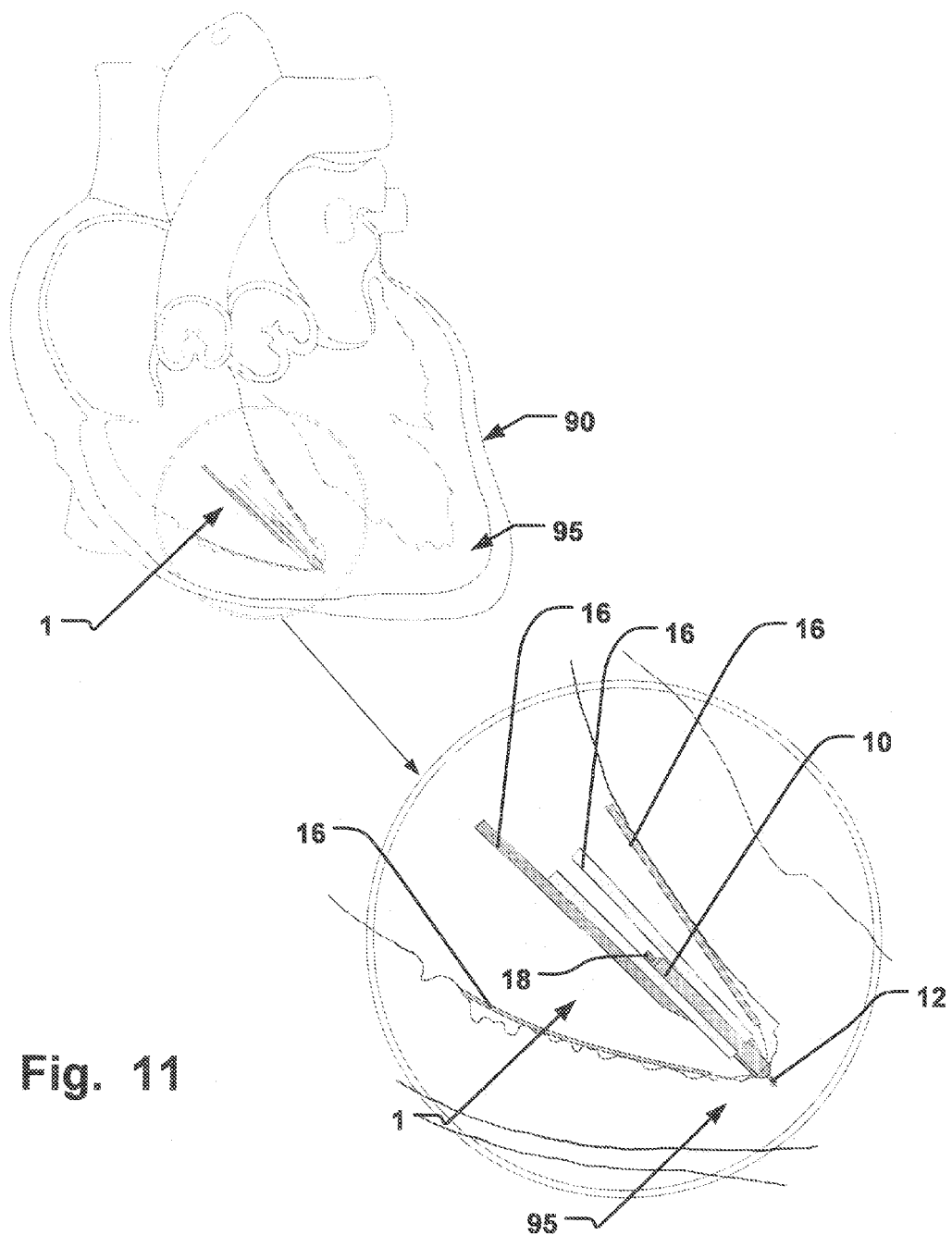
FIG. 11 depicts a schematic illustration of a "satellite" and "leaflets" implanted inside a heart.

FIG. 11 depicts a schematic illustration of a "satellite" 10 and "leaflets" 16 implanted inside a heart 90. More particularly, the system 1 is shown implanted inside the ventricle surrounded by heart muscle tissue 95.

The frequencies described in the cardiac application are within the Extremely Low Frequency (ELF) range and are about 0.7-3 Hz.

The deployment and the functionality of the main components of the system will now be explained in more detail. According to the current invention, a pacemaker (as well as any other cardiac implantable device) is mounted in the "satellite" container 10 containing piezoelectric power generator and power storage system. The "satellite" rear capturing unit 18 is attached to the capturing claw 20 at the end of the guidewire and encapsulated into a standard sheath. The whole system is loaded into the sheath in the transport position, advanced to its tip (see FIG. 3) and is introduced through the subclavian, jugular or cephalic vein. Either the 'stab' technique (inserting a needle until the subclavian vein is found) or a 'cut down' technique (separating superficial tissues until cephalic vein is found) is employed. Similarly, a "satellite" with cardiac resynchronization therapy (CRT) device can be passed through the femoral artery, aorta, aortic arch and ascending aorta to the left ventricular apex (a retrograde approach). In all cases hemostasis is achieved in one of the conventional manners.

Figure 3:
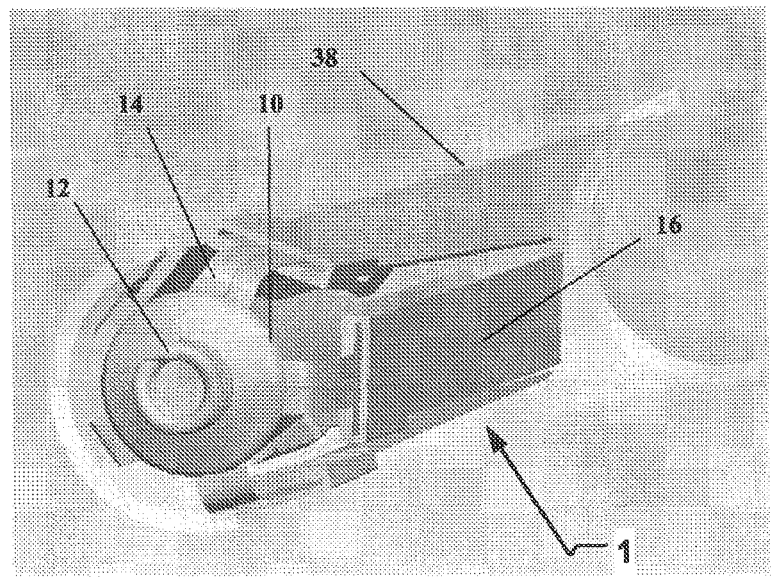
FIG. 3 depicts a schematic illustration of a transport view of a harnessing of natural power from the heart movement system.

FIG. 3 depicts a schematic illustration of a transport view of a harnessing of natural power from the heart movement system 1 in a collapsed transport configuration. As can be seen, the system 1 may be introduced into a sheath 38 of a catheter in a very compact manner. The bent connecting units 14 allow for a bending of the "leaflets" 16 in the longitudinal direction. Bending may be provided in a rearward configuration as shown in FIG. 3 for deployment. The system 1 has leaflets 16 bent backwards for delivery. Upon exiting the sheath 38, it is understood that the leaflets will move radially outwardly until and into tissue apposition with adjacent the cardiac tissue wall at the desired delivery site at the heart 90. Bending may be provided in a forward configuration (not shown) for retracting the system 1 back into the catheter. The connecting units 14 are both flexible, resilient. The connecting units 14 comprise in some embodiments, besides a mechanical connection, also electrical conductors for electrical connection of the piezoelectric leaflets 16 and the electric circuit of the system 1 in the satellite carrier unit 10. The electrical conductors may be advantageously integrated into the connection unit 14 into a single monolithic aggregate. The latter embodiment of connection unit 14 is particularly compact contributing to the miniaturization of the system 1.

The guidewire with the "satellite" is then passed down the vein or artery to the desired position inside the ventricle—normally the ventricular apex. The "satellite" is finally fixed on the endocardial wall with the help of the screw on its front surface and guidewire manipulations. Then the guidewire is released and the sheath is withdrawn from the body. The released "leaflets" 16 are pressed to their positions on the ventricle walls by virtue of the SMA rods 14 bridging the "leaflets" with the "satellite" and turning from bendable (martensite) state corresponding to the transport position into rigid springy (austenite) state and press the "leaflets" to the heart interior surface due to their shape memory properties, as shown in FIG. 1 and FIG. 2.

At this moment the piezoelectric power generator starts working accumulating the power of the heart movement in the electric power storage capacitor 22. Below we describe the routine and standard task to transform the charge stored in the capacitor 22 into the DC current for pacemaker consumption. When the capacitor is full the comparator 24 and a voltage regulator 26 are ready to provide the predefined DC current to the pacemaker. As the voltage reaches the predefined upper limit, the comparator permits the charge to flow from the capacitor through the regulator. The last delivers the predefined DC current to the pacemaker. The screw 12 being surrounded by myocardial tissue also performs the role of the pacing electrode.

Once the voltage on the storage capacitor drops below the predefined lower limit, the comparator interrupts the current through the regulator, and the circuit once again starts storing the piezoelectric power generator's output. All voltage levels on the comparator and regulator are programmable using feedback resistors.

Figure 6:
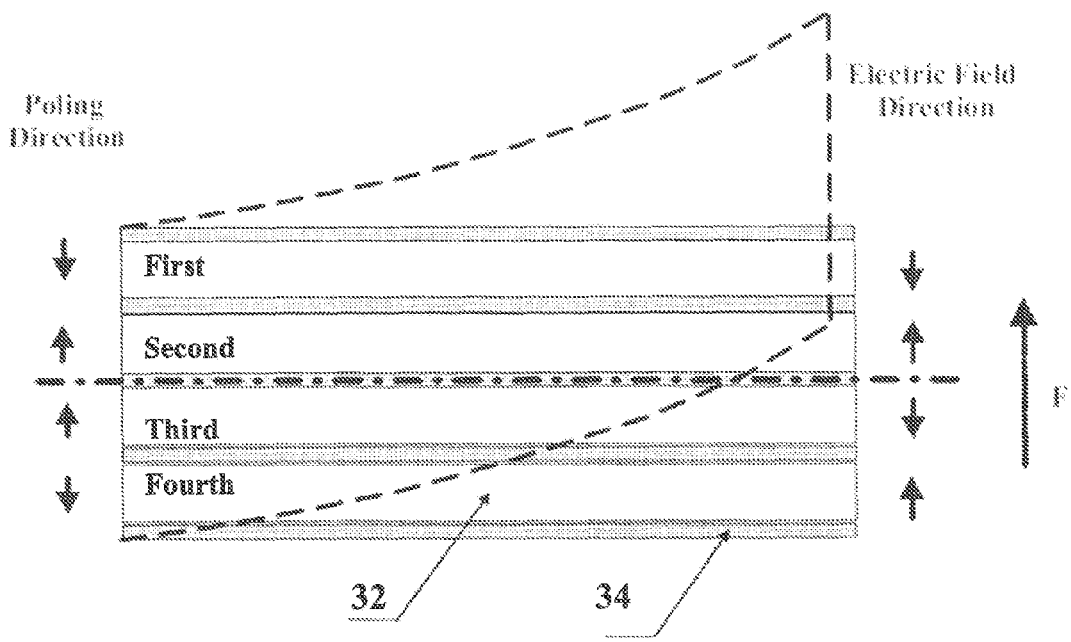
FIG. 6 shows the interior "leaflet" structure: Monolithic multiple layer bender type piezoelectric element.

The power generation process in each of the "leaflets" 16 can be described as follows:

each "leaflet" comprises monolithic multiple layer bender type elastic piezoelectric elements, each piezoelectric element is built of multiple monomorphes 32 generating electric power under the bending mechanical moment provided by the heart movement, as shown in FIG. 6. In order to achieve the maximal efficiency of the power generation, each of the monomorphes 32 is divided from its neighbors by electrodes 34 and polarized in the way that the vectors of polarization of the two neighboring layers are anti-linear, but the vectors of polarization of the two central layers divided by an isolator plate 36 are collinear, see FIG. 7. In each "leaflet" all electrodes are divided into two groups and all monomorphes possess two electrodes belonging to different groups.

In this manner, a particularly advantageous and efficient harvesting of energy is provided. Embodiments provide thus for harvesting of energy in the range needed for continuously operating a pacemaker or similar implanted device without the need for a battery. This provides in turn for very compact carrier units.

In order to achieve the above polarization properties, a special method of polarizing the monomorphes' 32 was developed. The method comprises the steps of a. Separating the groups of the electrodes 34 (not containing the one belonging to the isolator plate plane 36) into two groups lying above and below the isolator plate plane;

b. Sequentially polarizing the monomorphes lying above and below the isolator plate plane through application of DC power to each of the electrode groups containing the one lying in the isolator plate plane 36;

c. Alternatively, simultaneously polarizing the monomorphes 32 through the application of opposite potential DC to each of the monomorph groups, while the group of electrodes containing the one lying in the isolator plate plane 36 is connected to the zero potential.

3D measurement of the heart muscle movement includes, for instance, measuring acceleration of the heart muscle and can be measured in different sections of the heart muscle simultaneously. Every element can be engaged simultaneously both in pacing and sensing. Thus we get the No. of ECG channels corresponding to the No. of "leaflets".

Additionally, ECG may be measured to provide corresponding information related to the electrical triggering and distribution of the triggering signal prior to the actual heart muscle movement. In this manner defects in both muscular action and the electrical triggering system can be identified by suitable algorithms.

Figure 10:
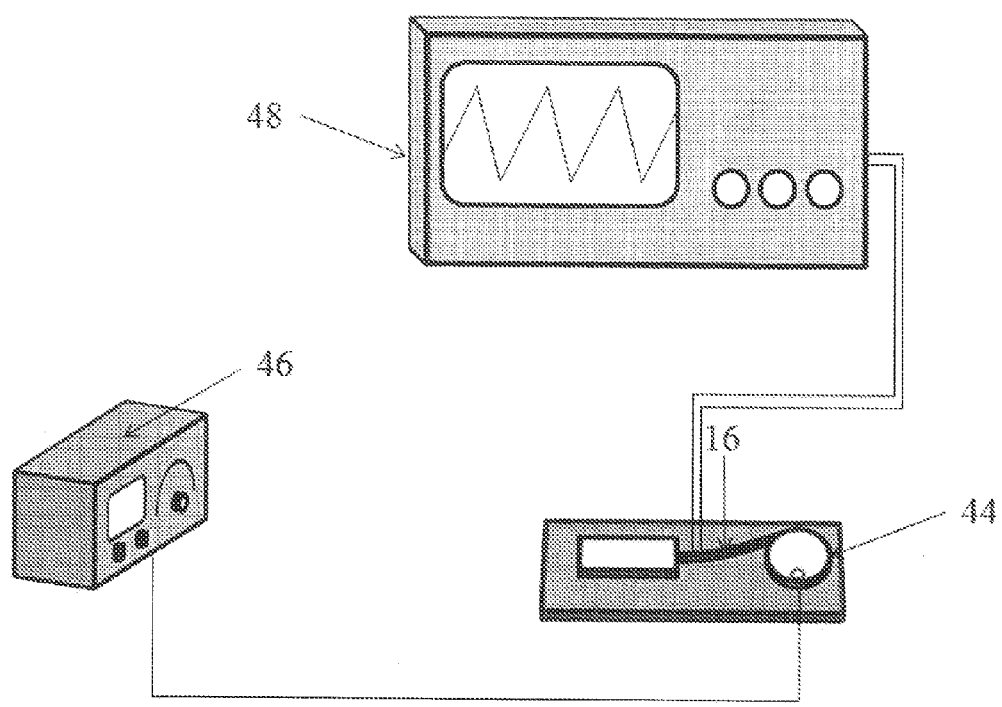
FIG. 10 depicts a schematic illustration of an experiment modelling pacemaker "leaflet" movement inside the heart.

An experiment modelling the pacemaker "leaflet" movement inside the heart is depicted in FIG. 10. An eccentric wheel 44 is electrically connected to a pulse generator 46. The pulse generator moves the eccentric wheel around its shifted centre 100-120 degrees left and right at about 1 Hz frequency. The eccentric wheel 44 generates bends piezoelectric "leaflet" 16 which is fixed with its rear end containing the electrodes and freely tangent to the wheel with its front end. The electric wires of the "leaflet" 16 are connected to an oscilloscope 48, showing a voltage 2.4 V at 0.7-1.3 Hz frequencies. The corresponding power 20 μW covers the 25 μW pacemaker requirements: 5 "leaflets" generate enough energy for 4 pacing cycles per second (source: Venkateswara Sarma Mallela, V. Ilankumaran and N. Srinivasa Rao, "Trends in Cardiac Pacemaker Batteries", Indian Pacing and Electrophysiology Journal (ISSN 0972-6292), 4(4): 201-212 (2004)). An experimental proof of the workability of the energy harvesting concept disclosed herein was thus made.

Finally, in emergency or other cases we describe here a method of "satellite" 10 extraction. It comprises (a) endovascularly introducing the sheath 38 with the claw 20 on the guidewire into the appropriate heart region containing the "satellite" 10

(b) orienting the claw 20 relative to the "satellite" rear capturing unit 18 through superposition of their marks visible on ultra-sound or fluoroscopy equipment (c) capturing the capturing unit 18 by the guidewire claw 20

(d) unscrewing the "satellite" 10 from the heart muscle with the help of the guidewire manipulation (e) introducing the "satellite" 10 back into the sheath 38 together with the "leaflets" 16

(f) extracting the catheter from the heart and the body.

The present invention has been described using a non-limiting detailed description of various embodiments thereof. It should be appreciated that the present invention is not limited by the above-described embodiments and that one ordinarily skilled in the art can make changes and modifications without deviation from the scope of the invention as will be defined below in the appended claims.

Figure 9:
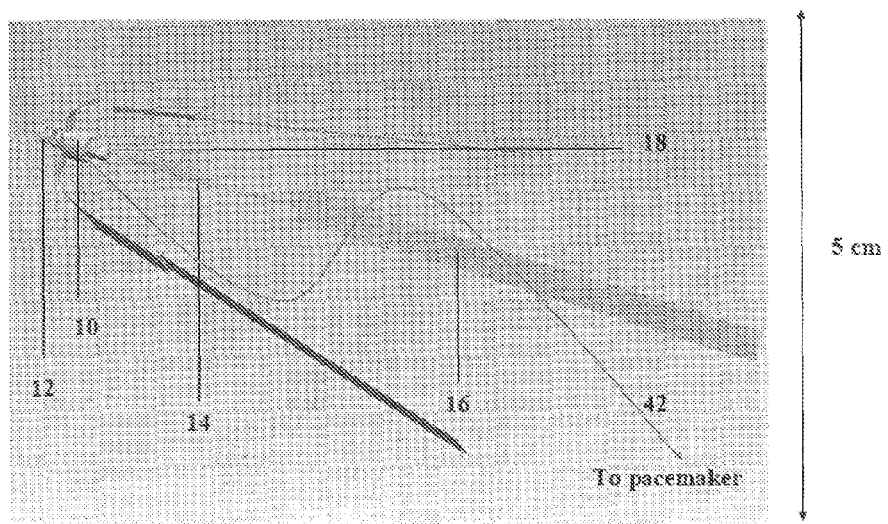
FIG. 9 depicts a schematic illustration of an alternative design of the system according to the present invention, where the pacemaker positioned outside the heart is used and the generator forms the unique complex with the pacing lead connected to pacemaker with a cable 42.

Below are listed some of the modifications, which are within the scope of invention as defined by the appended claims:

1. The invention can be used with the presently available two-fold pacemaker architectures. In this case the presence of additional source of energy, as the invented piezoelectric generator, considerably minimizes the original battery size and weight, recharges the battery and turns the overall system into the patient's life-long supporting device, see FIG. 9. In this case the invented piezoelectric generator forms a unique complex with the pacing lead and is connected through a wire to the connector block of a pacemaker. In this case the process of deployment of the system coincides with the regular implantation of pacemaker procedure through a subclavian jugular or cephalic vein.

2. Instead of Nitinol (nickel-titanium alloy) any Shape Memory Alloy with appropriate properties can be used, pacemaker can be substituted by Automatic Cardio Defibrillator or any other implantable device.

3. Furthermore, the invention can be used for development of power saving or transformation devices as described above in the case of low frequency piezoelectric transformer based on cantilever bending vibrations.

It should also be appreciated that features disclosed in the foregoing description, and/or in the foregoing drawings and/or following claims both separately and in any combination thereof, be material for realizing the present invention in diverse forms thereof. When used in the following claims, the terms "comprise", "include", "have" and their conjugates mean, "including but not limited to".

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A system comprising at least one multiple layer bender type piezoelectric element,
    said at least one multiple layer bender type piezoelectric element comprising four monomorphes for generating electric power under a bending mechanical moment, arranged in a first layer, a second layer, a third layer, and a fourth layer,
    said second layer and said third layer are two central layers, which are arranged between said first layer and said fourth layer, and are divided by an isolator plate,
    said first layer is arranged adjacent said second layer, and which are first neighbouring layers,
    said third layer is arranged adjacent said fourth layer, and which are second neighboring layers,
    wherein each of said four monomorphes is separated from its neighbours by electrodes and is polarized in such a way that vectors of polarization of the monomorphes of said first neighbouring layers are anti-linear and the monomorphes of said second neighbouring layers are anti-linear, and, in such a way that vectors of polarization of said two central layers are collinear.

2. The system of claim 1, wherein said system is entirely deployable inside a heart and said system further comprises:
    a piezoelectric power generator, a power storage unit, a control unit, and an electrically operated medical device operatively connected to each other and arranged in a carrier unit,
    wherein:
    said piezoelectric power generator comprises a plurality of piezoelectric elastic elongate rod units, said elongate rod units comprise monolithic multiple layer bender type piezoelectric elements configured for apposition to said heart muscle for generating electric power from movement of said heart muscle and for providing sensor signals related to a 3D movement of said heart muscle, and resilient connecting units are arranged between said elongate rod units and said carrier unit for providing a pretension towards said heart muscle for supporting said apposition.

3. The system of claim 2, wherein said connecting units are mounted on an edge of said carrier unit and have a first bendable state for delivery of said system inside a catheter to said heart.

4. The system of claim 3, wherein said connecting units have a second rigid resilient state when released from said catheter for pressing the piezoelectric elastic elongate rod units to the heart interior surface.

5. The system of claim 2, wherein said connecting units are initially shaped to reproduce an interior geometry of an interior heart region where said carrier unit is to be implanted.

6. The system of claim 2, wherein said resilient connecting units are shape memory alloy rods and wherein said first configuration for said transport position is a martensite state thereof, and said second rigid springy state is an austenite state thereof.

7. The system of claim 2, wherein said piezoelectric elastic elongate rod units are piezoceramic units.

8. The system of claim 2, wherein said piezoelectric elastic elongate rod units comprise pacing electrodes for stimulating respective heart regions according to results of obtained heart activity sensing.

9. The system of claim 2, wherein, in each piezoelectric elastic elongate rod unit, all electrodes are divided into two groups and all monomorphes possess two electrodes belonging to different groups.

10. The system of claim 2, wherein said piezoelectric elastic elongate rod units are arranged both as power suppliers and as sensors of overall 3D heart movements.

11. The system of claim 1, wherein said piezoelectric element is a piezoelectric elastic elongate rod unit with four layers in which all electrodes are divided into two groups and all monomorphes possess two electrodes belonging to different groups.

12. The system of claim 11, wherein at least one pair of said piezoelectric elastic elongate rod units is separated by a passive isolator layer that forms a low frequency lowering piezoelectric transformer based on cantilever bending vibrations, whereas the first piezoelectric elastic elongate rod unit of said pair is an output actuator for transforming electrical energy into mechanical energy in vibration form, while the second piezoelectric elastic elongate rod unit of said pair is an input unit for reconverting mechanical energy into electrical energy.

13. A method for harvesting power from movement of a heart muscle using the system of claim 2, said method comprising:

providing said system, positioning said system in a heart comprising said heart muscle, and bending said plurality of piezoelectric elastic elongate rod units in apposition to said heart muscle and thereby generating electric power from said movement of said heart muscle.

14. The method of claim 13, and further comprising providing sensor signals related to a 3D movement of said heart muscle by said monolithic multiple layer bender type piezoelectric elements.

15. A method for operating the system of claim 2, said method comprising:

generating power from said heart muscle movement by bending of said piezoelectric elastic elongate rod units by said heart muscle movement and providing energy from said piezoelectric power generator to said power storage unit and said electrically operated medical device, wherein said plurality of piezoelectric elastic elongate rod units are in apposition to said heart muscle.

16. A method for delivering the system of claim 2 to said heart, said method comprising:

providing the system of claim 2;

deploying said carrier unit inside a sheath and reversibly attaching said carrier by means of a proximal end unit to a capturing unit arranged at a distal end of a guidewire of said sheath;

manipulating said guidewire to endovascularly transport said carrier unit to said heart;

orienting said carrier unit inside said heart in the way that said piezoelectric elastic elongate rod units are in apposition with a heart muscle surface;

anchoring said carrier unit into the heart muscle;

releasing said carrier unit from said capturing unit and extracting the sheath from the heart and the body.

17. A method for extracting the system of claim 2 from a heart, said system being arranged in carrier unit anchored to heart muscle, said method comprising:

(a) endovascularly introducing a sheath containing a capturing unit on a distal end of a guidewire into said heart in a region where said carrier unit is anchored;

(b) orientating said capturing unit relative to said carrier unit;

(c) capturing of said carrier unit by said capturing unit;

(d) manipulating said guidewire to release the carrier unit from the heart muscle;

(e) introducing said carrier unit into said sheath together with said piezoelectric elastic elongate rod units attached to said carrier unit by resilient connecting elements, and (f) extracting the catheter from the heart and the body together with said carrier unit.

18. A method for manufacturing the system according to claim 2, said method comprising polarizing said piezoelectric elastic elongate rod units, wherein said polarizing comprises separating groups of said electrodes not belonging to a plane of said isolator plate into groups lying above and below said isolator plate plane.

19. The method of claim 18, and further comprising sequentially polarizing said monomorphes by applying opposite potential DC to each electrode group lying above and below the isolator plate plane.

20. The method of claim 18, and further comprising simultaneously polarizing said monomorphes by applying opposite potential DC to each of said monomorph groups while the electrodes lying in the isolator plate plane are connected to a zero potential.

* * * * *